US011395880B2

(12) United States Patent
Chang et al.

(10) Patent No.: US 11,395,880 B2
(45) Date of Patent: Jul. 26, 2022

(54) ELECTRONIC DRUG DELIVERY DEVICE

(71) Applicant: AMGEN INC., Thousand Oaks, CA (US)

(72) Inventors: Sung Keun Chang, Thousand Oaks, CA (US); Harold Dean, IV, Ventura, CA (US); Michael Friedman, Newbury Park, CA (US); Gordon Johnston, Dallas, TX (US); Neal Johnston, Dallas, TX (US)

(73) Assignee: AMGEN INC., Thousand Oaks, CA (US)

( * ) Notice: Subject to any disclaimer, the term of this patent is extended or adjusted under 35 U.S.C. 154(b) by 175 days.

(21) Appl. No.: 16/615,019

(22) PCT Filed: Jun. 22, 2018

(86) PCT No.: PCT/US2018/038914
§ 371 (c)(1),
(2) Date: Nov. 19, 2019

(87) PCT Pub. No.: WO2018/237225
PCT Pub. Date: Dec. 27, 2018

(65) Prior Publication Data
US 2020/0164145 A1 May 28, 2020

Related U.S. Application Data

(60) Provisional application No. 62/524,185, filed on Jun. 23, 2017.

(51) Int. Cl.
*A61M 5/20* (2006.01)
*A61M 5/32* (2006.01)

(52) U.S. Cl.
CPC ............ *A61M 5/20* (2013.01); *A61M 5/3202* (2013.01); *A61M 2005/202* (2013.01); *A61M 2205/50* (2013.01); *A61M 2205/8206* (2013.01)

(58) Field of Classification Search
CPC ........................ A61M 5/31565; A61M 5/3202
See application file for complete search history.

(56) References Cited

U.S. PATENT DOCUMENTS

| 5,176,646 A | 1/1993 | Kuroda |
| 5,509,905 A | 4/1996 | Michel |
| (Continued) | | |

FOREIGN PATENT DOCUMENTS

| WO | WO-2015187793 A1 | 12/2015 |
| WO | WO-2017100501 A1 | 6/2017 |

OTHER PUBLICATIONS

International Search Report for International Application No. PCT/US2018/038914, dated Oct. 16, 2018.
(Continued)

*Primary Examiner* — Emily L Schmidt
(74) *Attorney, Agent, or Firm* — Marshall, Gerstein & Borun LLP

(57) ABSTRACT

A drug delivery device includes a housing, a drug delivery assembly disposed within the housing along a longitudinal axis, and a cap defining a shell. At least one electronic component, a power source, and a switch assembly are at least partially disposed in and coupled to the cap. The switch assembly is movable along a plane orthogonal to the longitudinal axis of the drug delivery assembly to cause the power source to provide power to the electronic component. The device further includes an activation mechanism at least partially disposed in the cap. Upon urging the cap along the longitudinal axis in a direction away from the housing, the activation mechanism engages the switch assembly and
(Continued)

causes the switch assembly to move, thereby causing the power source to provide power to the at least one electronic component.

9 Claims, 12 Drawing Sheets

(56) References Cited

U.S. PATENT DOCUMENTS

| | | | |
|---|---|---|---|
| 5,544,647 A * | 8/1996 | Jewett | A61M 15/009 128/200.23 |
| 6,202,642 B1 * | 3/2001 | McKinnon | A61M 15/009 128/200.14 |
| 8,231,573 B2 | 7/2012 | Edwards et al. | |
| 8,361,026 B2 | 1/2013 | Edwards et al. | |
| 8,622,973 B2 | 1/2014 | Edwards et al. | |
| 8,801,679 B2 | 8/2014 | Iio et al. | |
| 9,278,177 B2 | 3/2016 | Edwards et al. | |
| 9,295,784 B2 | 3/2016 | Eggert et al. | |
| 2013/0060196 A1 * | 3/2013 | O'Connor | A61M 5/172 604/152 |
| 2016/0296716 A1 | 10/2016 | Cabiri et al. | |

OTHER PUBLICATIONS

Written Opinion for International Application No. PCT/US2018/038914, dated Oct. 16, 2018.

* cited by examiner

ELECTRONIC DRUG DELIVERY DEVICE

CROSS-REFERENCE TO RELATED APPLICATION

This is the United States National Phase of PCT/US18/38914, filed Jun. 22, 2018, which claims the priority benefit of U.S. Provisional Patent Application No. 62/524,185, filed Jun. 23, 2017, the entire contents of each of which are hereby incorporated herein by reference.

FIELD OF THE DISCLOSURE

The present disclosure generally relates injectors and, more particularly, to the powering of injectors having electronically assisted components.

BACKGROUND

Autoinjectors and on-body injectors offer several benefits in delivery of medicaments and/or therapeutics. One of the benefits can include simplicity of use, as compared with traditional methods of delivery using, for example, conventional syringes.

Even with the use of autoinjectors, patients may experience challenges during the initial use of the drug delivery device. For example, the user may be uncertain as to whether the medication inside the drug delivery device is the correct medication prescribed for them. The user may be uncertain as to whether the medication has expired and/or whether the injection should be delayed after a drug delivery device has been removed from cold storage, such as in a refrigerator. The user may also be uncertain if the actions and their sequence correctly operate the drug delivery device. Even if the actions are performed in the proper sequence, the user may be uncertain as to whether the drug has been completely delivered and that the injection process is complete. Further, users oftentimes wish to perform as few steps as possible in the drug administration process. If additional steps are added to the drug administration process, it is less likely that the user will be fully compliant. As an example, for adherence tracking, products may require a QR Code or NFC tag to be scanned or activated. While these additional steps may provide a useful benefit to the user, they lengthen the total drug administration time, which may be undesirable to some users. Patients may have any number of additional concerns related to the administration of the drugs.

As a result of these and other uncertainties and concerns, systems and methods are often provided which include electronic components capable of assisting with the drug administration process. For example, systems and their corresponding approaches may include any number of sensors or devices capable of monitoring the drug delivery device and/or the surrounding environment to determine whether the drug may be comfortably administered. These systems may also communicate information to the user, healthcare providers, and other interested parties. Because of the use of any number of electronics, the device must be capable of providing power before, during, and/or after the drug administration process. Portable power devices such as batteries may have a limited life and thus difficulties may arise when providing power to the delivery devices after extended durations. Further, these systems can be large and complex, and may occupy a large amount of space within the autoinjector.

In some examples, the electronics, power sources, and/or activation mechanisms may all be stored in a cap of the autoinjector. The electronics may become activated upon removing the cap from the assembly. Current systems typically operate using any number of components that cooperate to depress a switch assembly to power electronic devices when the cap is removed. These systems oftentimes require substantial forces in order to fully depress the switch assembly, which may cause user discomfort when administering the medicament. For example, due to forces required to depress the switch and overcome any internal frictional forces from additional actuation devices and/or assemblies, the total overall force required to remove the cap may result in an uncomfortable medicament administration experience.

SUMMARY

In accordance with a first aspect, a drug delivery device includes a housing, a drug delivery assembly disposed within the housing along a longitudinal axis, and a cap defining a shell. At least one electronic component, a power source, and a switch assembly are at least partially disposed in and coupled to the cap. The switch assembly is movable along a plane orthogonal to the longitudinal axis of the drug delivery assembly to cause the power source to provide power to the electronic component. The device further includes an activation mechanism at least partially disposed in the cap. Upon urging the cap along the longitudinal axis in a direction away from the housing, the activation mechanism engages the switch assembly and causes the switch assembly to move, thereby causing the power source to provide power to the at least one electronic component.

In this aspect, the activation mechanism may include a sliding activation ring having a finger portion that engages the switch assembly upon the cap being urged away from the housing. The finger portion of the sliding activation ring may have a chamfered engaging surface that engages the switch assembly. Upon urging the cap along the longitudinal axis to a first position, the switch assembly may then move relative to the finger portion to engage the finger portion. Further, upon urging the cap along the longitudinal axis to a second position, the sliding activation ring may engage a cap coupling portion to be removed from the housing along with the cap. In some examples, the cap coupling portion may be a protrusion disposed on an inner surface of the cap.

In some of these examples, the finger portion of the sliding activation ring may include an angled or chamfered engaging surface which engages the switch assembly. This engagement and continued relative movement between the chamfered engaging surface and the switch assembly may cause the switch assembly to move.

In any of these examples, the sliding activation ring may further be adapted to prevent the drug delivery assembly from discharging while the cap at least partially covers a portion of the first end of the drug delivery assembly.

In some forms, the activation mechanism can include a resilient member having an engaging surface which engages the switch assembly when the cap is urged in the direction away from the housing. The resilient member may be in the form of a spring lever that is movable between a first, disengaged position and a second, engaged position. In these forms, when the cap is coupled to the housing, the first end of the drug delivery assembly urges the spring lever to the first, disengaged position. When the cap is urged away from the housing along the longitudinal axis to a first position, the spring lever moves to the second, engaged position to engage the switch assembly.

In accordance with a second aspect, a signal cap is provided for an autoinjector that includes a cap body defining a cap shell and being formed along a longitudinal axis, an electronic component, a power source, a switch assembly, and an activation mechanism. The electronic component is at least partially disposed in and coupled to the cap shell. Similarly, the power source is at least partially disposed in and operably coupled to the cap shell, and selectively powers the electronic component. The switch assembly is operably coupled between the electronic component and the power source, and is movable along a plane that is orthogonal to the longitudinal axis of the cap body to cause the power source to provide power to the electronic component. The activation mechanism is additionally at least partially disposed in the cap shell. Upon urging the cap body along the longitudinal axis to a first position, the activation mechanism engages the switch assembly and causes the switch assembly to move, which causes the power source to provide power to the electronic component.

In accordance with a third aspect, an approach for triggering a switch assembly in a drug delivery device is provided. The drug delivery device can include a housing defining a shell and having a longitudinal axis, a drug delivery assembly disposed within the housing along the longitudinal axis of the housing, a cap defining a shell that removably couples to the housing, at least one electronic component at least partially disposed in and coupled to the cap, and a power source at least partially disposed in and coupled to the cap for selectively powering the at least one electronic component. The approach includes coupling a switch assembly to the at least one electronic component. The switch assembly is movable along a plane orthogonal to the longitudinal axis to cause the power source to provide power to the at least one electronic component. The approach further includes at least partially disposing an activation mechanism in the cap, and urging the cap along the longitudinal axis in a direction away from the housing. Upon urging the cap, the activation mechanism engages the switch assembly to cause the switch assembly to move, thereby causing the power source to provide power to the at least one electronic component.

BRIEF DESCRIPTION OF THE DRAWINGS

The above needs are at least partially met through provision of the electronic drug delivery device described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an electronic drug delivery device includes a housing defining a shell, a drug delivery assembly disposed within the housing along a longitudinal axis, and a cap defining a shell. At least one electronic component, a power source, and a switch assembly are at least partially disposed in and coupled to the cap. The switch assembly is movable along a plane orthogonal to the longitudinal axis to cause the power source to provide power to the electronic component. The device further includes an activation mechanism at least partially disposed in the cap. Upon urging the cap along the longitudinal axis in a direction away from the housing, the activation mechanism causes the switch assembly to move, thereby causing the power source to provide power to the at least one electronic component.

So configured, by converting axial movement when removing the cap from the housing into movement in an orthogonal direction, the drug delivery device may use a compact switch assembly that does not occupy a substantial amount of space. Further, the switch assembly does not require a high activation force necessary for actuation, which can in turn increase user comfort when preparing and administering the drug. This configuration also does not include any overtravel within the switch assembly, as all force and displacement tolerances required to fully depress the switch are located in the activation mechanism. Further, activation forces are minimized, and thus a user need not exert additional force to remove the cap from the injector housing. Further still, by using an entirely passive design, there is no additional user interaction necessary to activate the electronics beyond the current requirement of only removing the cap prior to administration of the drug.

Figure 1:
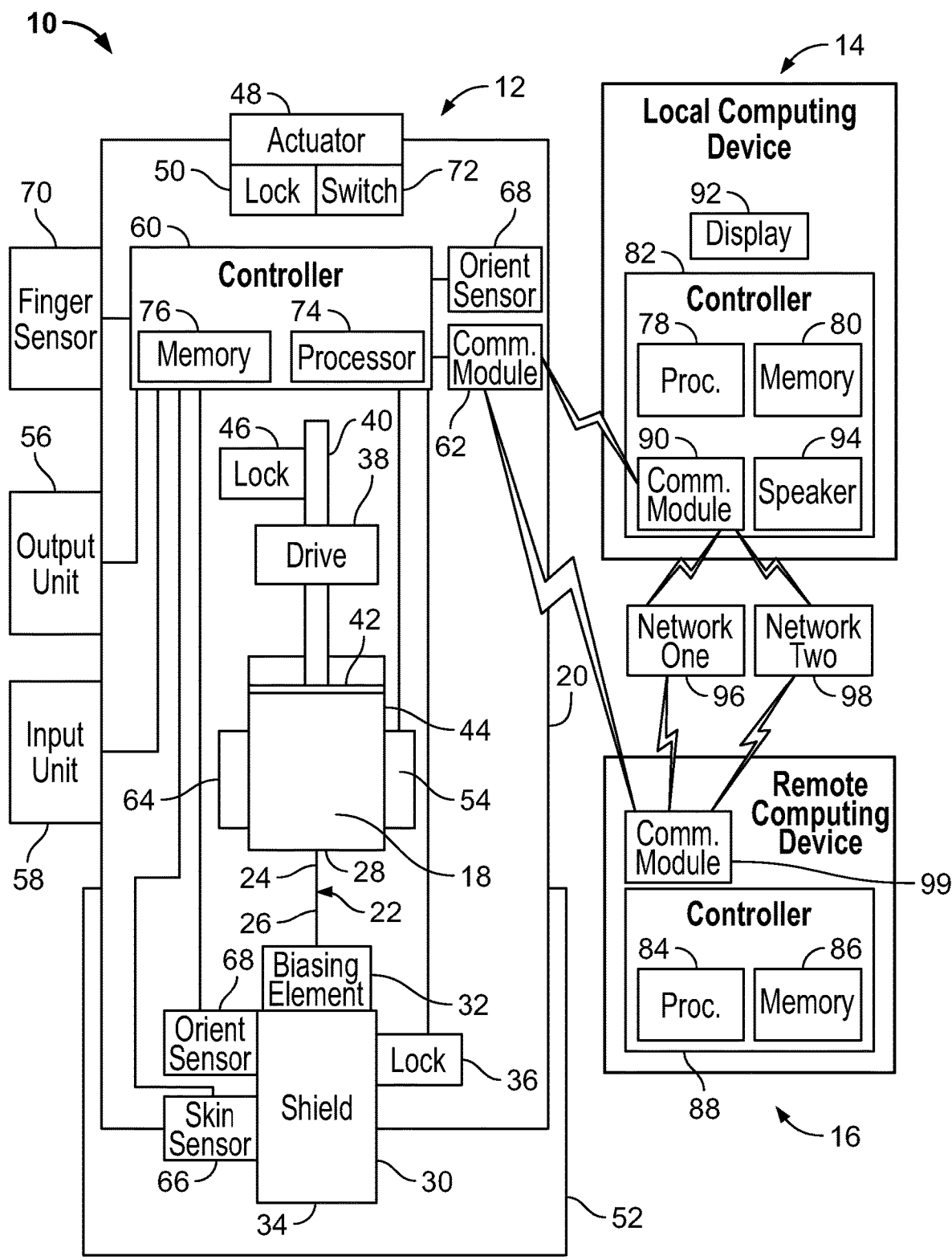
FIG. 1 illustrates a block diagram of an example system including a drug delivery device and a number of computing devices interconnected via a number of communication links and networks in accordance with various embodiments.

Referring now to the drawings, and in particular to FIG. 1, one generalized example of a system 10 is provided which includes a drug delivery device 12, a local computing device 14 and a remote computing device 16. While the system 10 includes both a local computing device 14 and a remote computing device 16, not all embodiments according to this disclosure include both a local computing device 14 and a remote computing device 16.

The drug delivery device 12 may be in the form of an autoinjector, and thus is adapted for hand-held use and application against the skin of the patient. The drug delivery device 12 includes a housing 18 in which are disposed assemblies or structures that introduce a delivery cannula into the patient, and that eject a drug or medicament from a reservoir 18 through the delivery cannula into the patient. According to certain embodiments, the same assemblies or structures that introduce the delivery cannula into the patient may also eject the drug or medicament from the reservoir through the delivery cannula into the patient. The drug delivery device 12 may also include assemblies or structures that connect the delivery cannula to the reservoir, that withdraw the delivery cannula into the housing 20 through an opening in the housing 20 (not illustrated), or that deploy other structures that will prevent contact with the delivery cannula once the delivery cannula has been removed from the patient. Any number of additional assemblies and structures are possible. The specific embodiment of the drug delivery device 12 discussed below is thus by way of example and not by way of limitation.

Accordingly, the drug delivery device 12 includes a reservoir 18 and a delivery cannula 22 having a first end 24 (e.g., a proximal end) that may be connected or connectable in fluid communication with the reservoir 18 and a second end 26 (e.g., a distal end) that may be inserted into a patient. The delivery cannula 22 may be, for example, a rigid needle having a beveled edge that may be sized such that the second end 26 of the needle 22 is received under the skin so as to deliver a subcutaneous injection of the medicament within the reservoir 18. The first end 24 of the needle 22 may be disposed through a wall 28 of the reservoir 18, and thus be connected in fluid communication with the reservoir 18. Alternatively, the first end 24 of the needle 22 may be disposed only partially through the wall 28 (which wall 28 may be a resalable septum or stopper, for example) such that the first end of the needle 22 may not be connected in fluid communication until the second end 26 of the needle 22 is inserted into the patient. In such a circumstance, the first end 24 of the needle 22 may thus be described as connectable in fluid communication with the reservoir 18, although it will be recognized that there are other mechanisms by which the first end 24 of the needle 22 may be connectable, but not connected, in fluid communication with the reservoir 18.

The drug delivery device 12 includes a shield 30 (e.g., a needle shield) that may be deployed at least after the injection has been completed to limit access to the second end 26 of the needle 22. According to certain embodiments, the shield 30 may have a biasing element 32 (such as a spring) that extends the shield 30 from the housing 20 such that a distal end 34 of the shield 30 extends beyond the second end 26 of the needle 22 except when the shield 30 is disposed against the skin and the insertion of the needle 22 is actuated. In fact, the insertion of the needle 22 may be actuated according to certain embodiments of the drug delivery device 12 by disposing the distal end 34 of the shield 30 on or against the skin of the patient.

The drug delivery device 12 may also include a lock 36 (e.g., a ratchet) that is coupled to the shield 30 and configured to limit or prevent movement of the shield 30 relative to the housing 20 of the drug delivery device 12 such that the distal end 34 of the shield 30 extends from the housing 20 a sufficient distance to limit or prevent contact with the second end 26 of the needle 22, for example, after the needle 22 has been removed or separated from the skin of the patient. In some embodiments, the lock 36 may be coupled to a controller (e.g., controller 60 described in more detail below) which can selectively activate or deactivate the lock 36 based on different types of information regarding the drug delivery device 12, including operational state information, condition information, and/or identity information, in accordance with one or more of the methods described above. When the lock 36 is activated by the controller 60, the lock 36 may be configured to limit or prevent movement of the needle shield 30 relative to the housing 20. When the lock 36 is deactivated by the controller 60, the lock 36 may be configured to allow movement of the needle shield 30 relative to the housing 20.

The drug delivery device 12 also includes at least one drive 38 that may be used to insert the second end 26 of the needle 22 into the skin of the patient, and to eject the drug or medicament from the reservoir 18 through the delivery cannula 22 into the patient. The drive 38 may include one or more springs, according to certain embodiments. According to other embodiments, the drive 38 may include a source of pressurized gas or a source of a material that undergoes a phase change, such that the escaping gas or phase changing material provides a motive force that may be applied to the reservoir 18 to eject the drug therefrom. According to still other embodiments, the drive 38 may include an electromechanical system, such as may include a motor for example, although such an electromechanical system may be more appropriate for the on-body autoinjector or infuser described above. Other embodiments of the drive 38 are also possible.

In one embodiment, the drive 38 may be coupled to a plunger 40 and/or a stopper 42 (e.g., a wall) disposed in the reservoir 18 to move that stopper 42 in a distal direction toward the delivery cannula 22. In accordance with such an embodiment, the stopper 42 may be a stopper that is fixed to a distal end of the plunger 40 and received within a bore 44. The plunger 40, in conjunction with the drive 38, may move the stopper 42 along a longitudinal axis of the drug delivery device 12 through the bore 44 from a proximal end of the bore 44 to a distal end of the bore 44, and thereby eject the medicament from the reservoir 18.

In some embodiments, the drive 38 may also cooperate with the stopper 42 and/or the bore 44 to move the reservoir 18 relative to the housing 20 so as to move the second end 26 of the needle 22 relative to the housing 20 and into the patient. According to those embodiments wherein the drive 38 cooperates with the stopper 42, this may occur before the first end 24 of the needle 22 is in fluid communication with the reservoir 18. According to those embodiments wherein the drive cooperates with the bore 44, the drive may include one component (e.g., first spring) that cooperates with the bore 44 to move the reservoir 18 and needle 22 relative to the housing 20, and a second component (e.g., second spring) that cooperates with the stopper 42 to move the stopper 42 relative to the bore 44.

The drug delivery device 12 may also include a lock 46 that is coupled to the plunger 40 and configured to limit or prevent movement of the plunger 40 relative to the housing 20 of the drug delivery device 12 so that the stopper 42 cannot be advanced to discharge the medicament from the reservoir 18 to the patient. In some embodiments, the lock 46 may be coupled to a controller (e.g., controller 60 described in more detail below) which can selectively activate or deactivate the lock 46 based on different types of information regarding the drug delivery device 12, including operational state information, condition information, and/or identity information, in accordance with one or more of the methods described above. When the lock 46 is activated by the controller 60, the lock 46 may be configured to limit or prevent movement of the plunger 40 relative to the housing 20. When the lock 46 is deactivated by the controller 60, the lock 36 may be configured to allow movement of the plunger 40 relative to the housing 20.

The drive 20 may be associated with an actuator 48. The actuator 48 may activate the drive 38 to cause the drive 38 to insert the needle 22 and eject the drug from the reservoir 18 through the needle 22 into the patient. The actuator 48 may, according to certain embodiments, be the needle shield 30, as explained above. According to other embodiments, such as the one illustrated in FIG. 1, the actuator 48 may be a button that may be manually depressed by the user or patient once the drug delivery device 12 is placed disposed on or against the patient's skin. A lock 50 may be coupled to the actuator 48 and configured to limit or prevent movement of the actuator 48 so that the actuator 48 cannot be used to activate the drive 38. In some embodiments, the lock 50 may be coupled to a controller (e.g., controller 60 described in more detail below) which can selectively activate or deactivate the lock 50 based on different types of information regarding the drug delivery device 12, including operational state information, condition information, and/or identity information, in accordance with one or more of the methods described above. When the lock 50 is activated by the controller 60, the lock 50 may be configured to limit or prevent movement of the actuator 48 relative to the housing 20. When the lock 50 is deactivated by the controller 60, the lock 50 may be configured to allow movement of the actuator 48 relative to the housing 20.

The drug delivery device 12 may also include a removable sterile barrier or signal cap 52 that is disposed about one or more of a distal end of the housing 20, the needle shield 30, and the second end 26 of the delivery cannula 22. The signal cap 52 may be removably attached to the distal end of the housing 20 as shown in FIG. 1. In some embodiments, the signal cap 52 may form an interference or snap fit with the distal end of the housing 20. A frictional force associated with the interference or snap fit may be overcome by manually pulling the signal cap 52 in a direction away from a housing 20. The signal cap 52, when attached to the drug delivery device 12, may reduce the risk of contamination of the delivery cannula 22 and other elements disposed within the drug delivery device 12.

Additionally, the drug delivery device 12 may include a heating element 54 coupled to the exterior of the reservoir 18 and configured to warm the medicament inside the reservoir 18 through, for example, conductive heating. The heating element 54 may be coupled to the controller 60 so that the controller 60 can selectively activate or deactivate the heating element 54 based on different types of information regarding the drug delivery device 12, including operational state information, condition information, and/or identity information, in accordance with one or more of the methods described above. In some embodiments, the heating element 54 may include an electrically conductive coil that is wrapped around the exterior of the reservoir 18. In other embodiments, the heating element may include an electrically conductive coil wrapped around the cannula 22. Alternatively, or additionally, a cooling element (not illustrated) may be coupled to the reservoir 18 and controllable by the controller 60 in a manner similar to the heating element 54.

The drug delivery device 12 may also include an output unit 56 coupled to the housing 20 and configured to notify the patient or user of information related to the drug delivery device 12. The output unit 56 may be coupled to the controller 60 so that the controller 60 can selectively activate or deactivate the output unit 56 based on different types of information regarding the drug delivery device 12, including operational state information, condition information, and/or identity information, in accordance with one or more of the methods described above. The output unit 56 may be any device suitable for conveying information to the patient or user including a display (e.g., a liquid crystal display), a touchscreen, a light (e.g., a light emitting diode), a vibrator (e.g., an electro-mechanical vibrating element), a speaker, and/or an alarm, among other devices.

The drug delivery device 12 may also include an input unit 58 coupled to the housing 20 and configured to allow a user or patient to input information (e.g., password information) to be used by the controller 60. In some embodiments, the input unit 58, the output unit 56, and even the fingerprint sensor 70, may be a single device such as a touchscreen. In other embodiments, the input unit 58 may be a separate device from the output unit 56 such as a keyboard or button.

As illustrated in FIG. 1, the reservoir 18, the biasing element 32, the locks 36, 46, 50, the plunger 40, the stopper 42, and the drive 38, and the heating element 54 are disposed within the housing 20, along with at least part of the delivery cannula 22. Also disposed within the housing 20 is a controller 60, a communication module 62 (e.g., a wireless transmitter), and at least one sensor or switch. According to the embodiment illustrated in FIG. 1, four sensors are included: a temperature sensor 64, a skin sensor 66, at least one orientation sensor 68, and a fingerprint sensor 70. The sensors 64, 66, 68, and 70 may each generate sensor data (e.g., raw or unprocessed data) related to a respective measured property or aspect of the drug delivery device 12. The sensor data may be representative of at least one of a condition or operational state of the drug delivery device 12. Additionally, the drug delivery device 12 includes a switch 72. The controller 60 is coupled to the communication module 62, the locks 36, 46, 50, the sensors 64, 66, 68, 70, the heating element 54, the fingerprint sensor 70, the output unit 56, the input unit 58, and the switch 72. The controller 60 may be configured to process the sensor data generated by the sensors 64, 66, 68, and 70 to determine a condition and/or operational state of the drug delivery device 12. The controller 60, the communication module 62, one or more of the sensors 64, 66, 68, 70 and the switch 72 may be packaged together as a single module, or each component may be fabricated separately and coupled once the components are disposed within the housing 20. According to certain embodiments, each electrical component may be integrated into the structure of the device 12 associated with that electrical component (e.g., the sensors 66 and 68 may be integrated into the shield 30). In some embodiments, the controller 60, the communication module 62, one or more of the sensors 64, 66, 68, 70, and/or the switch 72 may be packaged together inside the signal cap 52.

The controller 60 may include at least one processor 74 (e.g., a microprocessor) and a memory 76 (e.g., a random access memory (RAM), a non-volatile memory such as a hard disk, a flash memory, a removable memory, a non-removable memory, etc.). The controller 60 may also include or be coupled to a power supply, e.g. a battery. The processor 74 may be programmed to carry out the actions that the controller 60 is adapted to perform and the memory 76 may include one or more tangible non-transitory readable memories having executable, computer-readable, non-transitory instructions stored thereon, which instructions when executed by the at least one processor 74 may cause the at least one processor 74 to carry out the actions that the controller 60 is adapted to perform. Alternatively, the controller 60 may include other circuitry that carries out the actions that the controller is adapted to perform.

The memory 76 may store the identity information discussed above. The identity information may be stored in the memory 76 prior to the start of execution of any of the methods discussed above. The identity information may include, by way of example and not by way of limitation, a unique identifier, the name of the drug, the dosage, an expiration date, and information regarding the identity of the patient for whom the drug was prescribed. With this information, the controller 60 or a local computing device (e.g., a smartphone) may make a determination regarding the patient that is about to receive the drug, and provide appropriate informational and/or instructional prompts. As an alternative to memory 76, the identity information may be contained in a QR code label or RFID tag associated with the drug delivery device 12.

The communication module 62 may be any of a number of different communication modules used to communicate with a local computing device (e.g., a smartphone) and/or a remote computing device (e.g., a server operated by the device manufacturer). According to one embodiment, the communication module 62 may be a Bluetooth and/or Bluetooth Low Energy module that is on-board with the controller 60. The communication module 62 is used to transmit information from the drug delivery device 12 to the local computing device 14 and/or the remote computing device 16. Alternatively, other wireless protocols, whether short range or long range, may be used by the communication module 62. Short range protocols may include for example radio-frequency identification (RFID), Zigbee, Wi-Fi, near field communication (NFC), and others, whereas long range protocols may include mobile telephony protocols, cellular, GSM, CDMA, LTE, WiMAX, EDGE, 3G, 4G, HSPA+, EV-DO, DECT, UMTS, iDEN, SMS messaging, satellite communication protocols, AMPS etc. In fact, the communication may be sent along a hardwired connection, rather than using the electromagnetic (EM) spectrum. As defined herein, a communication transmitted and/or received between the module 62, the local computing device, and/or the remote computing device may be in the form of a hardwired signal or EM signal or a pattern of such signals, for example.

The temperature sensor 64 may be disposed proximate to the reservoir 18 so that the temperature of the drug in the reservoir 18 may be determined. Alternatively, the temperature sensor 64 may simply be disposed in the housing 20, so that an approximate temperature of the drug in the reservoir 18 and of the drug delivery device 12 generally may be determined. According to an embodiment, the temperature sensor 64 may be an on-board temperature sensor 64 attached to the processor 74.

The skin sensor 66 may be attached to or associated with the shield 30 to determine when the drug delivery device 12 is disposed on or against the patient's skin. According to one embodiment, the skin sensor 66 is a pressure sensor. According to other embodiments, the skin sensor 66 may be a capacitance sensor, resistance sensor, or inductance sensor. The skin sensor 66 or the switch 72 (which is attached to or associated with the actuator 48) may be used to determine when the drug delivery device 12 is activated or actuated, depending on the design and operation of the drug delivery device 12 that is used to actuate the drive 38, in accordance with the discussion above. It may also be the case that a signal from the skin sensor 64 is used to determine that the drug delivery device 12 has been activated even when the shield 30 is not used as the actual actuator, the underlying assumption being that the movement of the shield 30 is necessarily related to the actuation of the device 12.

The orientation sensors 68, of which there may be at least two as illustrated, may be associated with the shield 30 (or that portion of the housing 20 adjacent the shield 30) and the controller 60 (which may be, as illustrated, disposed at the other end of the drug delivery device 12 or the housing 20 from the shield 30). The orientation sensors 68 may be magnetometers, for example. In particular, the orientation sensor 68 associated with the controller 60 may be an on-board magnetometer. The orientation sensors 68 may be used to determine the orientation of the drug delivery device 12 (in particular, the housing 20) relative to the injection site (or more particularly, relative to the placement of the drug delivery device 12 on or against the patient's skin).

It will be recognized that the arrangement of the components of the drug delivery device 12 within the housing 20 is but one embodiment of this disclosure. For example, certain components of the drug delivery device 12 may be disposed outside the drug delivery device 12.

According to this embodiment, the drug delivery device 12 may include the housing 20, the reservoir 18, the needle 22, the shield 30, the biasing element 32, the lock 36, the drive 38, and the button 48. Furthermore, the sensors 66, 68 and the switch 72 may be disposed within the housing 20. The fingerprint sensor 70, the output unit 56, and the input unit 58 may be disposed on the exterior of the module 38 so that a user or patient can interact with them.

The separation of the controller 60, communication module 62 and other components into a module may permit the module to be used with multiple instances of the drug delivery device 12. In this regard, the module may be considered to be the reusable portion of the drug delivery device 12/module combination (which may be referred to as the drug delivery device 12 for purposes of this disclosure), while the drug delivery device 12 may be considered to be the disposable portion of the drug delivery device 12. By isolating the more expensive components into the reusable module and the less expensive components (including certain sensors) into the disposable drug delivery device 12, the overall cost of the autoinjector may be optimized. This arrangement of the components in the module and the drug delivery device 12 may also facilitate the manufacture and sterilization of the drug delivery device 12 and module.

The local computing device 14 may be in the form of at least one computing device including at least one processor 78 (e.g., microprocessor) and a memory 80 (e.g., a random access memory (RAM), a non-volatile memory such as a hard disk, a flash memory, a removable memory, a non-removable memory, etc.). The at least one processor 78 and the memory 80 may be incorporated into a controller 82 of the local computing device 14 and/or may be configured separately. Likewise, the remote computing device 16 may be in the form of at least one computing device including at least one processor 84 (e.g., microprocessor) and memory 86 (e.g., a random access memory (RAM), a non-volatile memory such as a hard disk, a flash memory, a removable memory, a non-removable memory, etc.). The at least one processor 84 and the memory 86 may be incorporated into a controller 88 of the local computing device 14 and/or may be configured separately. The memories 80, 86 may include one or more tangible non-transitory computer-readable memories having computer-executable instructions stored thereon (for example, in the form of a custom Mobile Application, or an App for short, or other software module).

According to the illustrated embodiment, the local computing device 14 is a mobile computing device (e.g., a smartphone, smart watch, tablet computer, etc.) while the remote computing device 16 is a server. In some embodiments, the local computing device 14 can include generally any computing device capable of processing data and being synched to and in communication with the drug delivery device 12 such as, for example, a smart wearable device, a personal computer, a laptop computer, a smart television, a smart appliance, a smart automobile, a networked computer, etc. According to other embodiments, the local computing device 14 may be a dedicated device such as a hub or gateway that can establish a communication link with the communication module 62 and potentially the remote computing device 16, where communication with the remote computing device 16 is necessary or desirable.

The local computing device 14 may further include a communication module 90 for wireless communication with the communication module 62 of the drug delivery device 12, for example by using Bluetooth/Bluetooth Low Energy protocol. Alternatively, other wireless protocols may be used by the communication module 62, such as radio-frequency identification (RFID), Zigbee, WI-Fi, near field communication (NFC), cellular, and others. The local computing device 14 may also include a display 92 to be used to communicate instructions to the user. The local computing device 14 may include other output devices other than the display 92 to communicate with the user, such as a speaker 94 for example. The speaker 94 may be controlled by the processor(s) 78 to provide an audible form of the instructions displayed in written form on the display 92.

The local computing device 14 may also include one or more communication modules, which may be the same as or different from the communication module 90, that may be used to communicate with one or more networks 96, 98. For example, the network 96 may be a wireless radio frequency network, such as a cellular mobile device network, while the network 98 may be a network of computing devices, such as the Internet. The networks 96, 98 may be in communication with each other, such that the local computing device 14 may communicate with the remote computing device 16 over the network 96, the network 98 or a combination of the networks 96, 98. The remote computing device 84 may include a communication module 99 to receive communications from the networks 96, 98.

While the terms "local" and "remote" have been used to describe the local computing device 14 and the remote computing device 16, these terms have not been selected to require a particular spatial or geographical distance between the devices 14, 16. Instead, the terms have been used to suggest a relative proximity to the user, and the fact that the remote computing device 16 is not required to be at the same physical location as the user and the drug delivery device 12. According to certain embodiments, it is possible, even likely, that the remote computing device 16 may be located in a different geographic location than the user and the drug delivery device 12, for example a different city, state or country.

The local computing device 14 and the remote computing device 16 are each separate from, and spaced apart from, the drug delivery device 12 and therefore may each be considered to be an "external computing device" relative to the drug delivery device 12.

Turning to FIGS. 2-5, a drug delivery device 100 is provided. The drug delivery device 100 may be in the form of an autoinjector, and thus configured for hand-held use and application against the skin of the patient. The drug delivery device 100 may include some or all of the same components as the drug delivery device 12 described above in connection with FIG. 1. The drug delivery device 100 may include a housing 102 which defines a shell that is formed along a longitudinal axis "A." A number of assemblies or structures are disposed within the housing 102. For example, a drug delivery assembly 104 may be at least partially disposed along the longitudinal axis that introduces a delivery cannula into a patient and that ejects a drug or medicament from a reservoir through the delivery cannula into the patient. The drug delivery assembly 104 may have a first end 104*a* and a second end 104*b*.

The drug delivery device 100 may further include a cap or signal cap 110 that defines a shell and is removably coupled to the housing 102. When coupled to the housing 102, the cap 110 at least partially covers a portion of the first end 104*a* of the drug delivery assembly 104. A number of components are at least partially disposed within the cap 110. With reference to FIGS. 3-6*b*, the drug delivery device 100 may also include at least one electronic component 120 which may be in the form of an electronic board having any number of components disposed thereon, a power source 122 that selectively powers the electronic component 120, and a switch assembly 130 (which, in the illustrated examples, is a rotatable switch assembly), each of which may be at least partially disposed in the cap 110. It is understood that any number of electronic components 120 may be used, and may include any combination of components previously stated with regards to FIG. 1. For example, the controller 60, the memory 76, the processor 74, the communication module 62 (e.g., a Bluetooth module, a Bluetooth Low Energy module, etc.), the skin sensor 66, the orientation sensor 68, the fingerprint sensor 70, the temperature sensor 64, the output unit 56, and/or the input unit 58 may be housed (e.g., embedded) within and/or coupled to the cap 110. In some examples, the electronic component 120 may generate data representative of at least one of a condition and an operational state of the drug delivery device and may further transmit that data to a processing unit.

The cap 110 may also serve as a removable sterile barrier which reduces the risk of contamination of the delivery cannula and other elements within the housing 102 prior to use of the drug delivery device 100. The cap 110 may be formed by a tubular member 111 and a cover member 112 that covers an open end of the tubular member 111. In some examples, the tubular member 111 and the cover member 112 may be integrally formed as a single unitary structure, or alternatively, formed as separate components which are adhered or mechanically interconnected to each other. With brief reference to FIGS. 8 and 9, an inner surface 111a of the tubular member 111 may include any number of cap coupling or catching protrusions 111b.

The tubular member 111 may be disposed about (e.g., surround) the first end 104a of the drug delivery assembly 104, and may removably attach the cap 110 to the housing 102. In some examples, the housing 102 may include a tab or protrusion 102a that mates with a corresponding notch (not shown) located on an inner sidewall of the tubular member 111 to secure the cap 110 to the housing 102. In some embodiments, the cap 110 may form an interference or snap fit with the housing 102. A frictional force associated with the interference or snap fit may be overcome by manually pulling or urging the cap 110 in a distal direction (i.e., along the longitudinal axis A) away from the housing 102. The interference or snap fit may be formed by configuring an inner diameter of the tubular member 111 to be slightly smaller than an outer diameter of the end of the housing 102. The tubular member 11 may further include a plurality of outwardly protruding ribs 111a designed to help a patient grip the tubular member 111 to detach it from the housing 102. The ribs 111a may be useful to elderly and disabled patients who have below average gripping strength.

The cover member 112 may be fixed to a distal end of the tubular member 111 and may completely cover an opening formed at the distal end of the tubular member 111. A distal end surface of the cover member 112 may be planar such that the drug delivery device 100 can be disposed on planar surface in an upright configuration without tipping or falling over. Also, an outer peripheral portion of the cover member 112 may be wider than an outer peripheral portion of the tubular member 111 such that a ledge or overhang 112a is formed at the interface between the cover member 112 and the tubular member 111. This ledge 112a may help prevent a patient's fingers from slipping over the cover member 112 when trying to pull the cap 110 off of the housing 102.

The cap 110 can be designed for single, one-time use, or for multiple uses. In embodiments of the cap 110 being constructed of multiple, distinct pieces, the cap 110 may be assembled by fitting each of the members separately around the housing 102 and then fixing the members together with an adhesive. In an alternative embodiment, the members may be hinged together in a clam shell arrangement. In such an alternative embodiment, after removing the cap 110 from the housing 102, it may be possible to re-attach the cap 110 to the housing 102 (or the housing of another drug delivery device) by opening the members like a clam shell and fitting them around the distal end of the housing 102. The non-hinged ends of the members may include a locking mechanism (e.g., mating locking tabs and/or slots) so that the members can be secured to each other after they are secured around the housing 102. Substantial cost savings may be realized by the reusable configuration of the cap 110 since the electronic component or components 120 coupled to the cap 110 can be used more than once. In still further embodiments, the cap 110 may be manufactured in one piece, and then installed axially onto the housing 102 of the drug delivery device 100.

Figure 4:
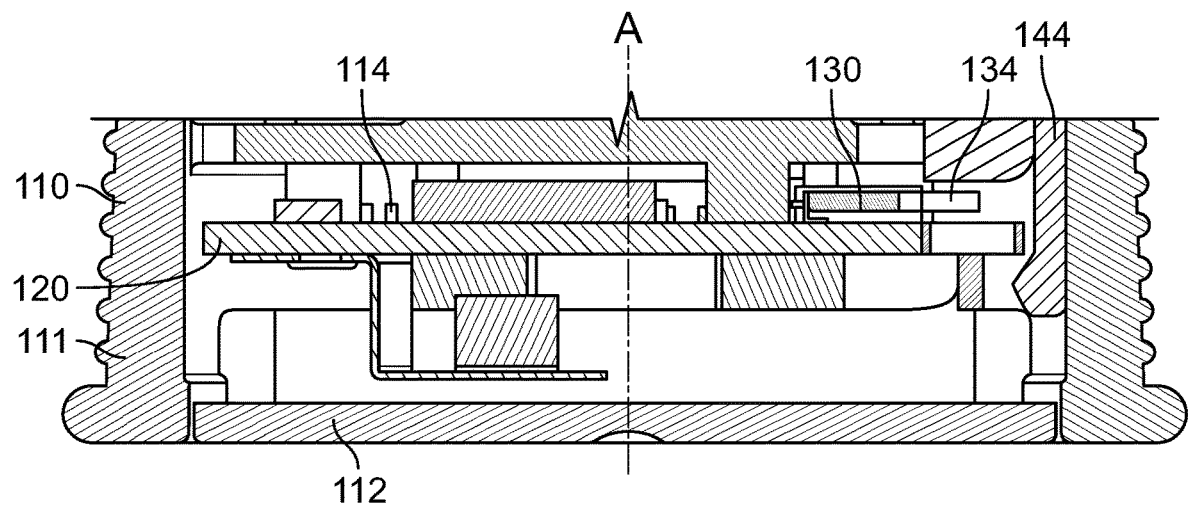
FIG. 4 illustrates a cross sectional view of a portion of the removable cap for the drug delivery device in accordance with various embodiments.
Figure 5:
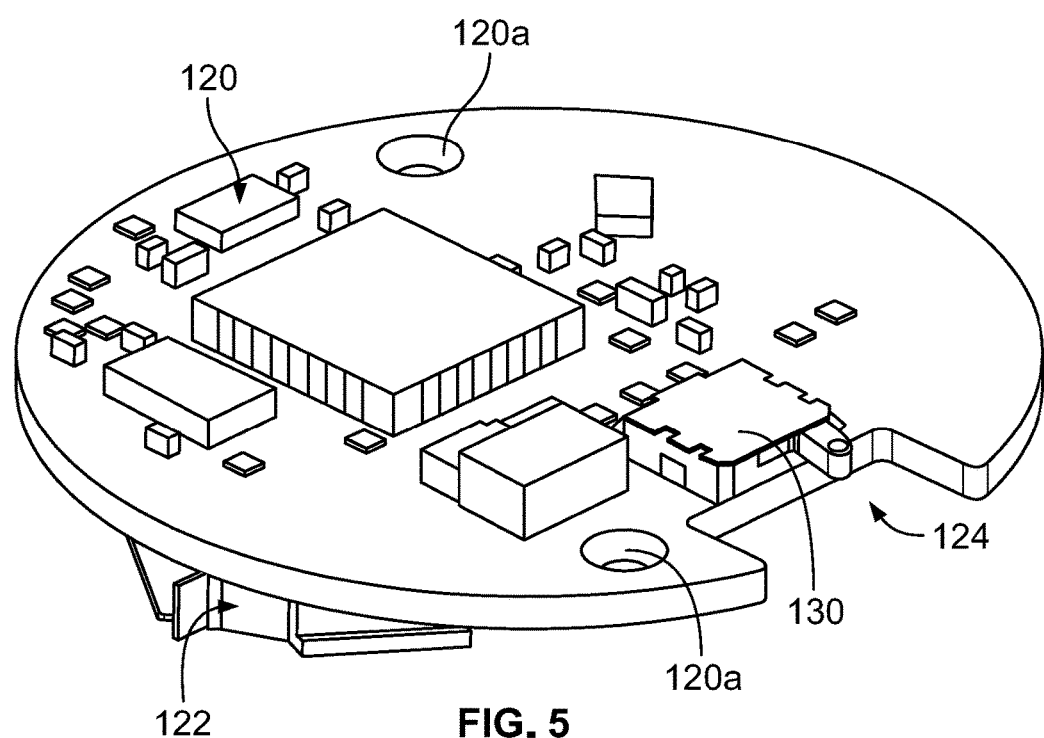
FIG. 5 illustrates a perspective view of an example electronic component and a switch assembly for the drug delivery device in accordance with various embodiments.
Figure 6A:
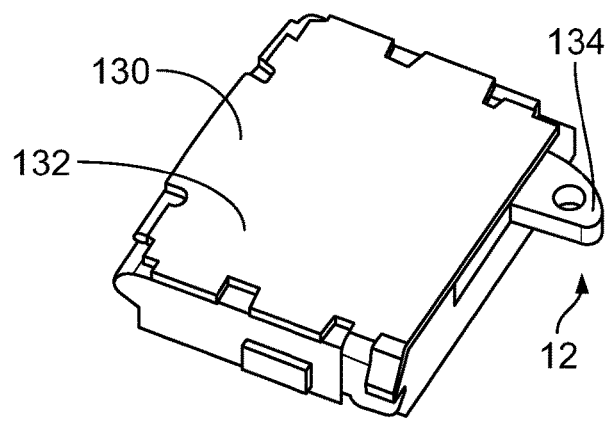
FIGS. 6a & 6b illustrate perspective and top plan views, respectively, of the example switch assembly for the drug delivery device in accordance with various embodiments.
Figure 6B:
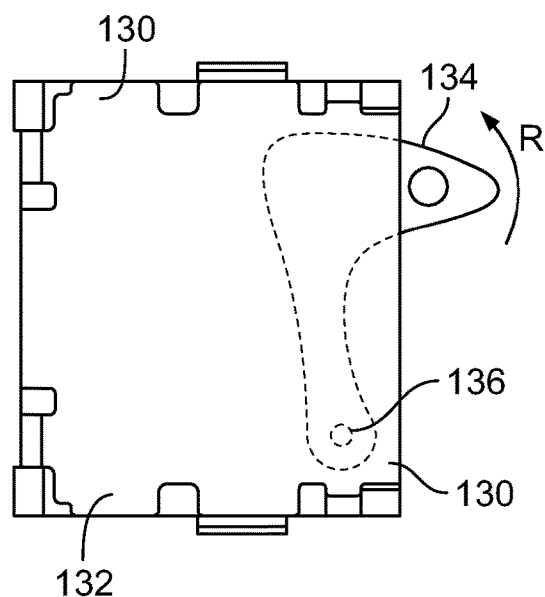

Turning to FIGS. 4-6b, the electronic component 120 and the rotatable switch assembly 130 are illustrated. The rotatable switch assembly 130 is coupled to the electronic component 120 and the power source 122, and causes the power source 122 to provide power to the electronic component 120. It is understood that in some examples, the power source 122 may be a battery or other device such as an energy harvesting device that uses a storage component such as a capacitor to provide power. As illustrated in FIG. 5, the electronic component 120 may have openings 120a disposed thereon to accommodate coupling to the cap 110. Specifically, the cap 110 may form a protrusion 114 to secure the electronic component 120 thereto. Other examples of coupling mechanisms are possible.

The rotatable switch assembly 130 includes a switch body 132 and a rotatable switch 134 that rotates about pivot 136 in a direction denoted by arrow "R". The rotatable switch 134 may be biased using a spring or any other mechanism (not shown) to maintain the rotatable switch 134 in the deactivated configuration illustrated in FIGS. 6a and 6b. The switch body 132 may also include a pivot or hinge member 136 that the rotatable switch 134 rotates around. In the illustrated example, the rotatable switch assembly 130 is in a deactivated state when the rotatable switch 134 protrudes from the switch body 132, and is in an activated state when the rotatable switch 134 is disposed within the switch body 132. As illustrated in FIG. 5, the thin wafer forming the electronic components 120 may have a cutout 124 that allows the rotatable switch 134 to project therefrom.

When the rotatable switch assembly 130 is disposed in the cap 110, the rotatable switch 134 rotates in a plane that is orthogonal to the longitudinal axis A. As such, when a user wishes to administer the drug, the cap 110 is removed by pulling or urging it axially along the longitudinal axis A in the direction away from the housing 102. This axial movement of the cap 110 causes the rotatable switch 134 to rotate in a direction that is orthogonal to the longitudinal axis A. It is understood that while the illustrated examples depict a rotatable switch assembly 130, any type of switch may be used that moves in a plane that is generally orthogonal to the longitudinal axis A. In these examples, the switch assembly may move in the generally orthogonal plane via non-rotational movement. For example, an axial switch may be used having generally linear movement into the switch body 132. Other examples are possible.

Figure 3:
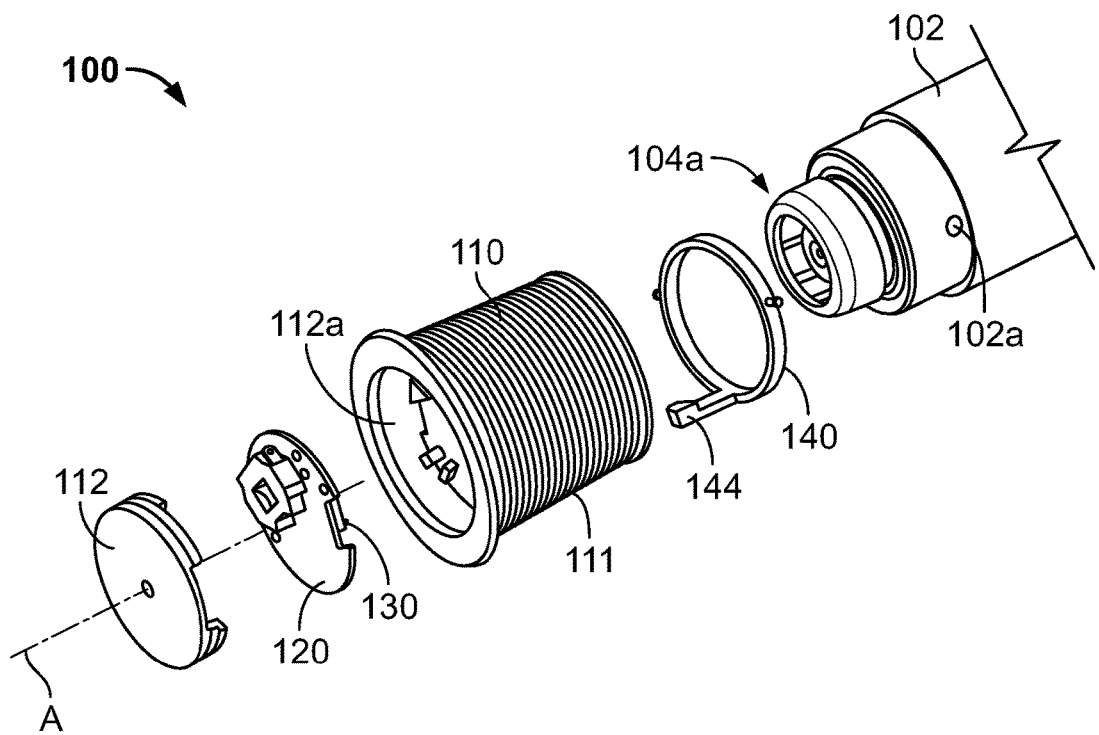
FIG. 3 illustrates a perspective view of an example removable cap for the drug delivery device in accordance with various embodiments.
Figure 7:
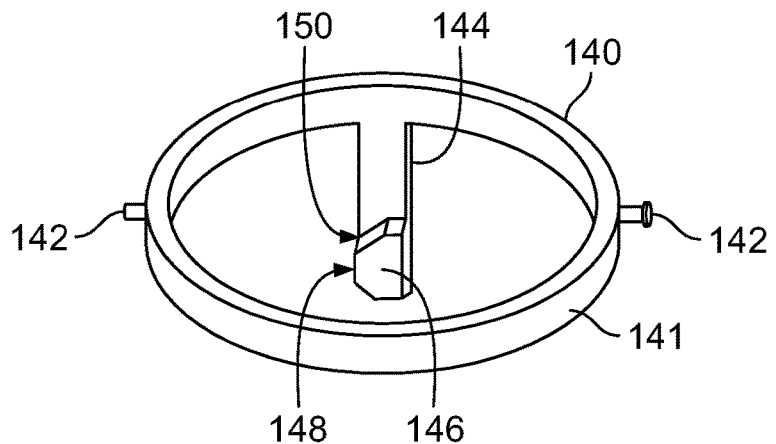
FIG. 7 illustrates a perspective view of an example activation mechanism for the drug delivery device in accordance with various embodiments.

With reference to FIGS. 3, 4, and 7, the device 100 further includes an activation mechanism 140. As illustrated in FIGS. 3 and 4 (which illustrates a portion of the activation mechanism 140), the activation mechanism 140 is also disposed within the cap 110 when coupled to the housing 102. The activation mechanism 140 may be generally ring-shaped and includes a body portion 141, any number of protrusions 142 extending from the body portion 141, and an activation finger 144 which extends from the body portion 141. In the illustrated example, the protrusions 142 may be used couple to the cap 110 and/or to limit axial motion of the activation mechanism 140 when disposed within the cap 110. In this example, the activation mechanism 140 is in the form of a sliding activation ring capable of axially moving within the cap 110.

Figure 8:
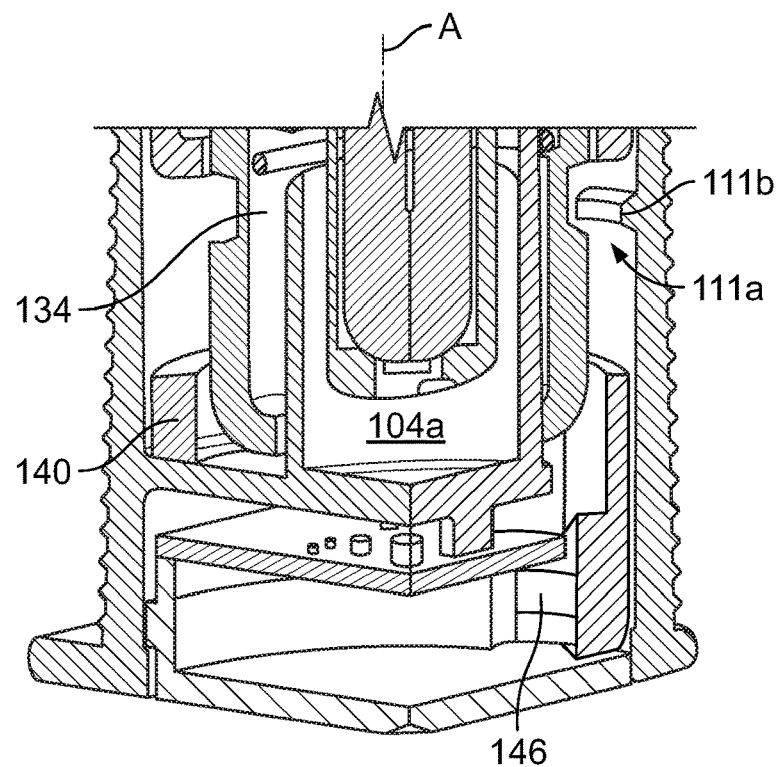
FIGS. 8 & 9 illustrate perspective views of the drug delivery device during removal of the removable cap in accordance with various embodiments.

The activation finger 144 may form a tab 146 having a first surface 148 and a second, angled or chamfered engaging surface 150. When the activation mechanism 140 is disposed within the cap 110, the activation finger 144 may extend from the body portion 141 in a generally parallel direction to the longitudinal axis A. With reference to FIGS. 4, 5, and 8, when the activation mechanism 140 is disposed within the cap 110, the tab 146 is positioned generally below the rotatable switch 134, and within the cutout 124 of the electronic component 120.

Figure 9:
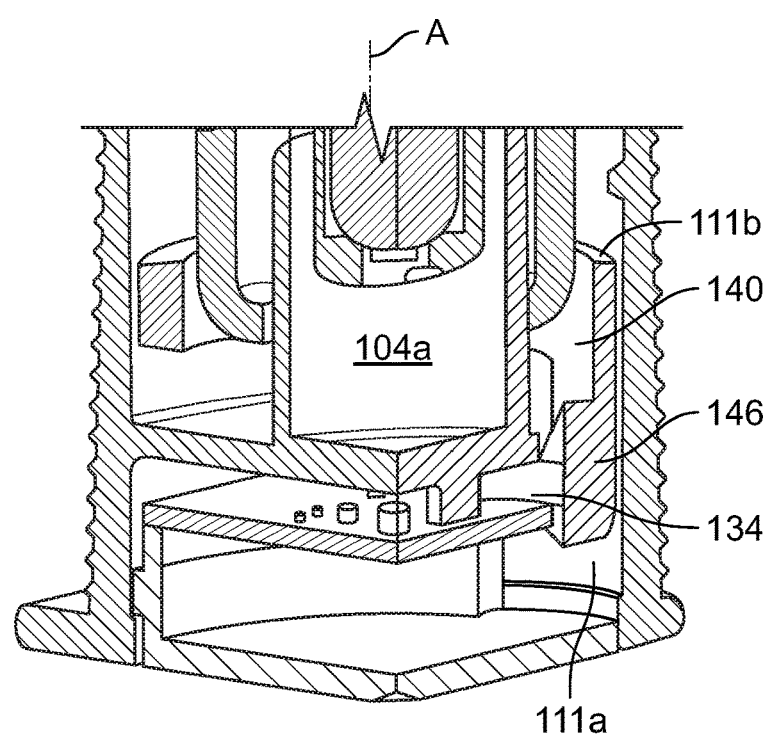
Figure 10:
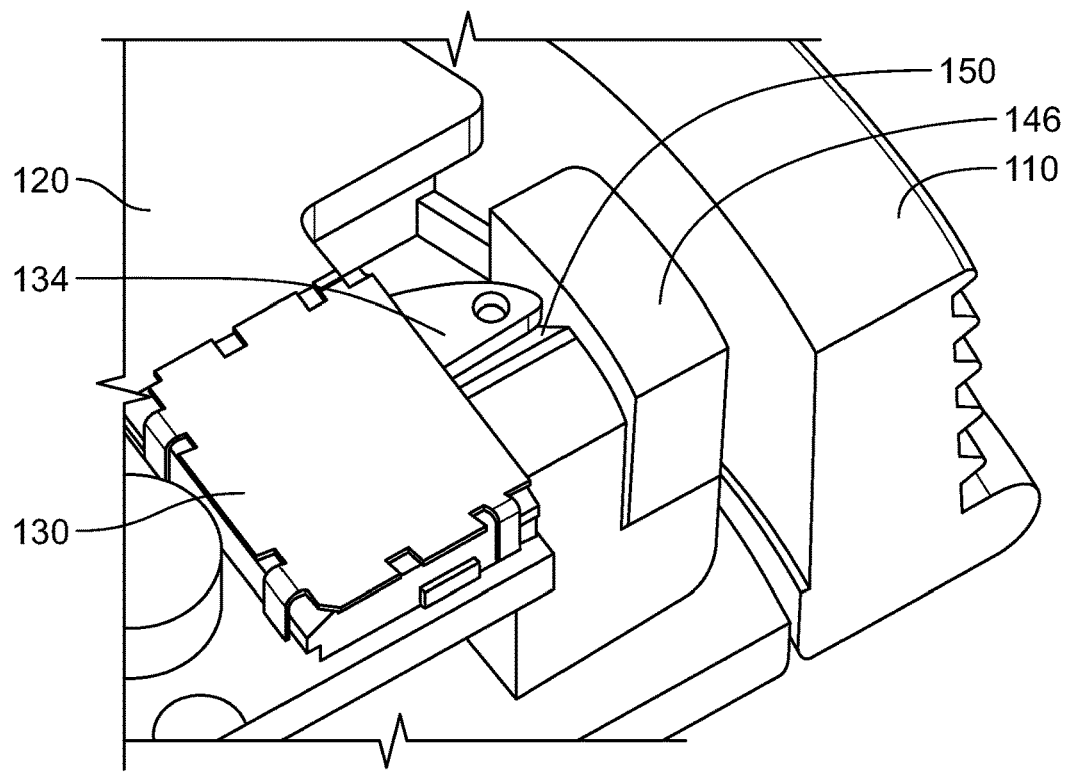
FIGS. 10-13 illustrate perspective views of an example interaction between the switch assembly and the activation mechanism during removal of the cap for the drug delivery device in accordance with various embodiments.

FIGS. 8-13 illustrate the cap 110 removal and electronic component 120 activation process. As illustrated in FIGS. 8 and 10, the cap 110 is coupled to the housing 102. As previously mentioned, in this configuration, the rotatable switch 134 is generally disposed above the tab 146 of the activation finger. Specifically, the rotatable switch 134 may be adjacent to or in contact with the angled surface 150. In this configuration, the rotatable switch 134 is in the deactivated configuration.

Figure 11:
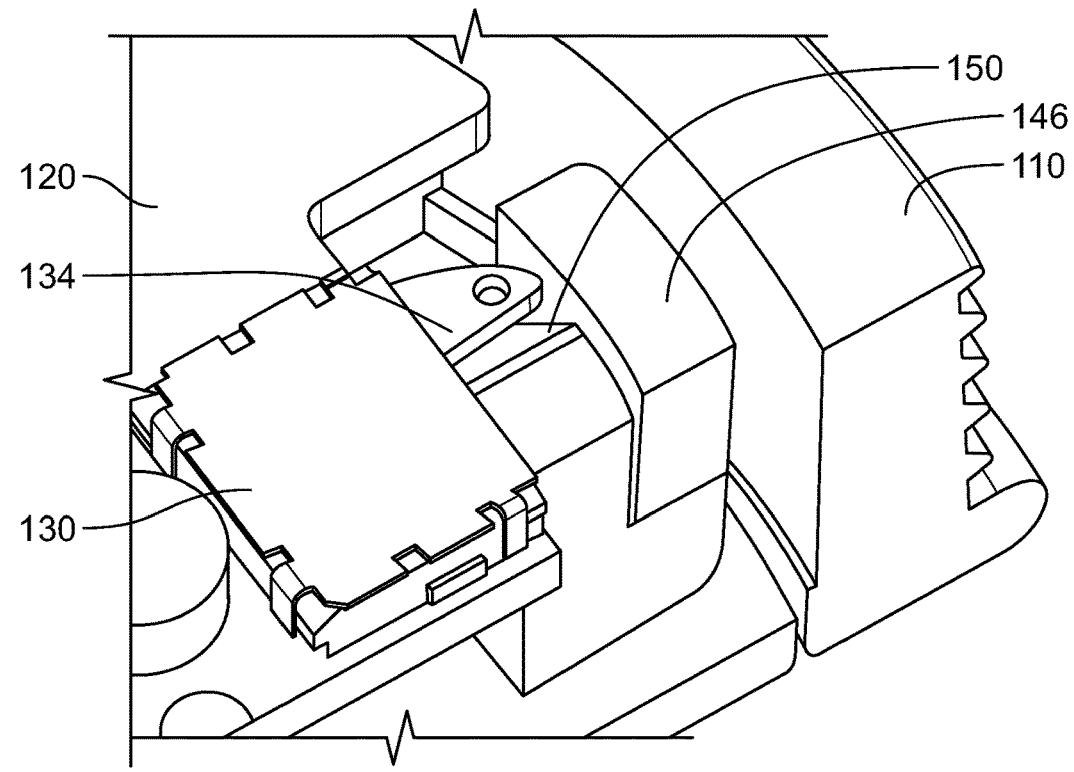

With reference to FIGS. 9 and 11, when it is desired to deliver the medicament to the patient, the user first urges the cap 110 along the longitudinal axis A to a first position in a direction away from the housing 102. In other words, the user begins to pull the cap 110 off of the housing 102. Because the electronic component 120, and thus the rotatable switch assembly 130, are coupled to the cap 110, these components also move away from the housing 102 and the activation mechanism 140 (which remains stationary relative to the cap 110) when the cap 110 is pulled. At this point, the angled surface 150 of the activation finger 144 begins to contact the rotation switch 134. This contact causes the rotation switch 134 to begin rotating about the pivot 136 inwardly towards the switch body 132. As mentioned, this rotation is along a plane that is orthogonal to the direction in which the cap 110 is pulled (e.g., along the longitudinal axis A).

Figure 12:
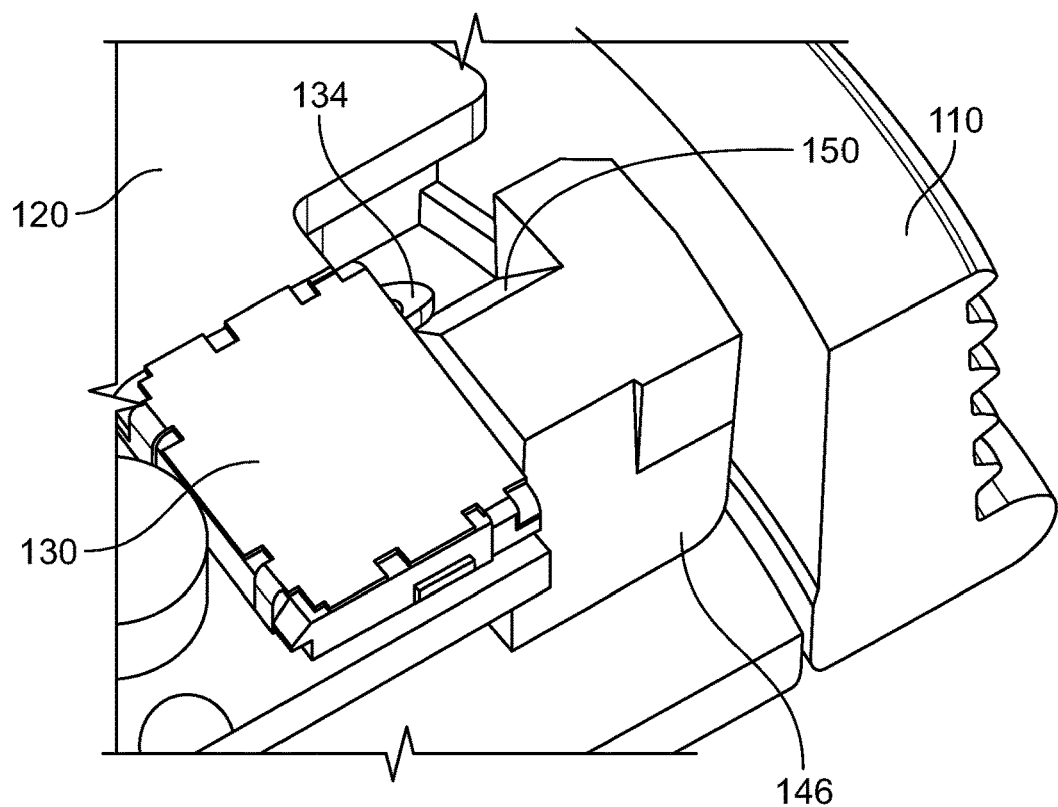
Figure 13:
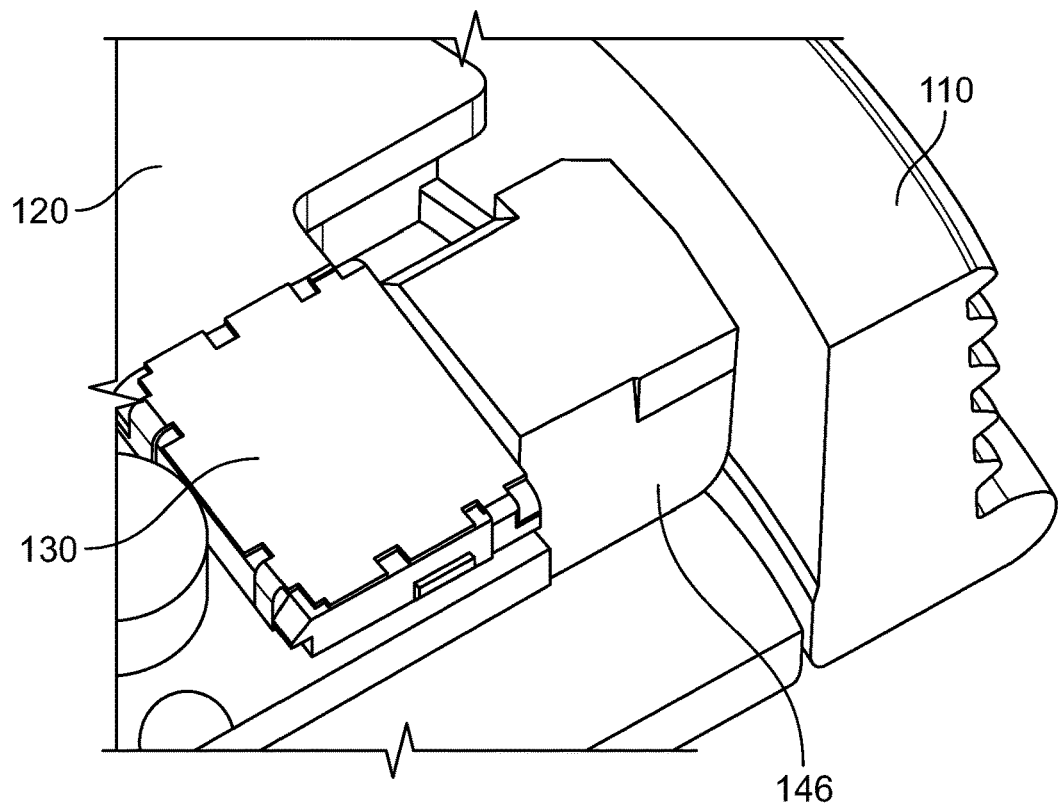
Figure 14:
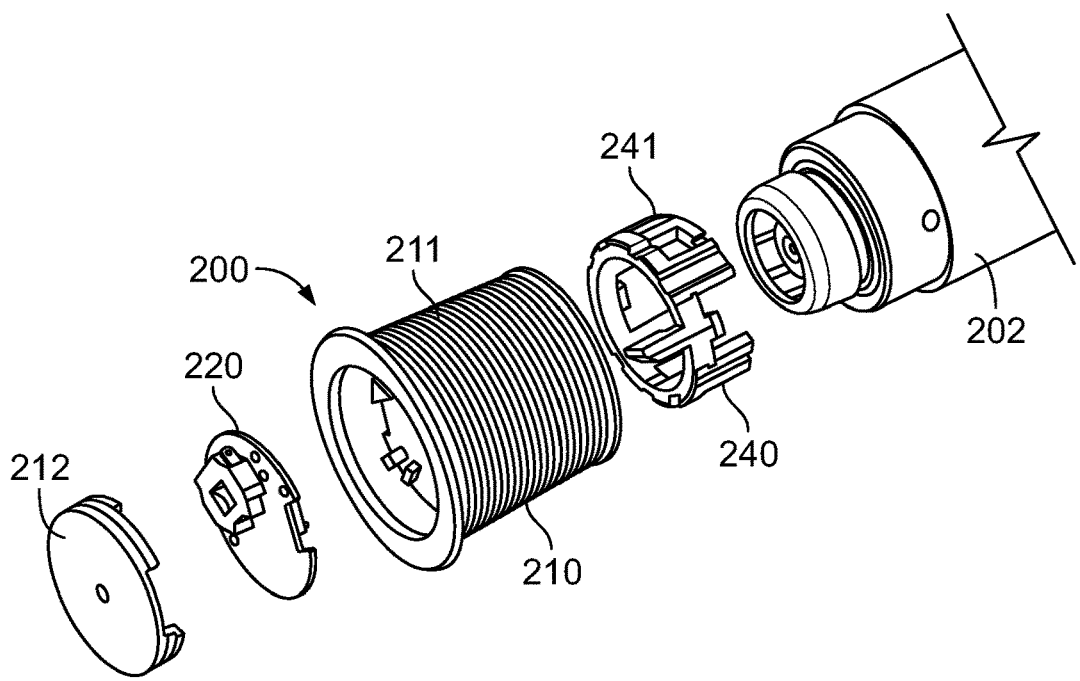
FIG. 14 illustrates a perspective view of an alternate removable cap for the drug delivery device in accordance with various embodiments.
Figure 15:
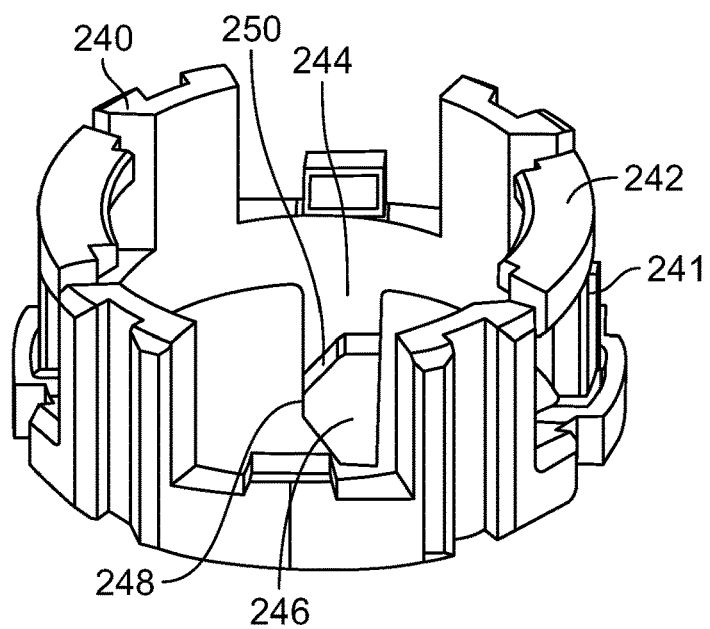
FIG. 15 illustrates a perspective view of an alternate activation mechanism for the drug delivery device in accordance with various embodiments.

As illustrated in FIG. 12, continued pulling of the cap 110 away from the housing 102 causes the rotation switch 134 to continue contacting the angled surface 150, thus the rotation switch 134 continues rotating inwardly into the switch body 132. As illustrated in FIG. 13, the rotation switch 134 is fully positioned within the switch body 132, and is in the activated configuration which causes the power source 122 to power the electronic component 120. At this point, a portion of the rotation switch 134 may be in contact with the first surface 148 of the tab 146 of the activation finger 144. So configured, continued urging of the cap 110 away from the housing causes the rotation switch 134 to remain in the activated configuration.

In this example, continued pulling of the cap 110 away from the housing 102 to a second position causes the catching protrusions 111b to contact the protrusions 142 on the body portion 141 of the activation mechanism 140. This contact causes the activation mechanism 140 to begin moving away from the housing 102 with the remaining components disposed within the cap 110 (i.e., the electronic component 120, the rotatable switch assembly 130, and any additional components). In this configuration, the first surface 148 remains in contact with the rotating switch 134 and retains the rotating switch 134 in this position, thus, the rotatable switch assembly 130 remains activated when the cap 110 is removed from the housing 102.

As illustrated in FIGS. 14-19, an alternate drug delivery device 200 is provided. The drug delivery device 200 includes similar features and elements as the drug delivery device 100, and thus have reference numerals with identical two-digit suffixes as those in the drug delivery device 100 of FIGS. 1-13. As such, for the sake of brevity, similar components will not be described in detail.

In the drug delivery device 200, the activation mechanism 240 also acts as a locking mechanism to restrict the drug delivery device 200 from accidental discharge prior to removal of the cap 210 from the housing 202. The activation mechanism 240 includes a body portion 241, a locking protrusion 242 extending inwardly from the body portion 241, an activation finger 244 extending from the body portion 241 which interacts with a needle guard 205 having a channel 205a of the drug delivery assembly 204.

Figure 16:
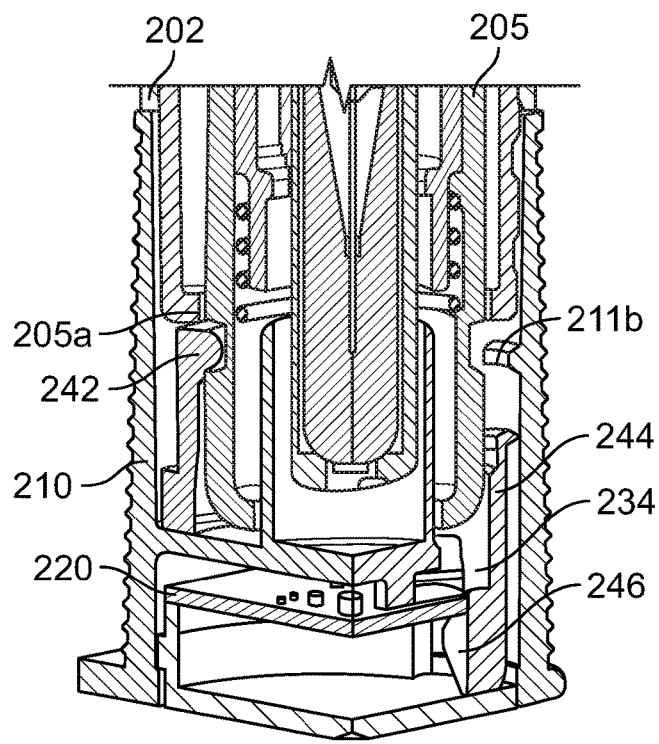
FIGS. 16-19 illustrate perspective views of the drug delivery device of FIGS. 14 & 15 during removal of the removable cap in accordance with various embodiments.

As illustrated in FIG. 16, prior to removal of the cap 210, the housing 202 and needle guard 205 are fixed. The locking protrusion 242 is nestled in the channel 205a to prevent the needle guard 205 from moving axially into the housing 202. As such, the risk of accidental discharge of the medicament and/or unintentionally sticking the needle into the user is mitigated.

Figure 17:
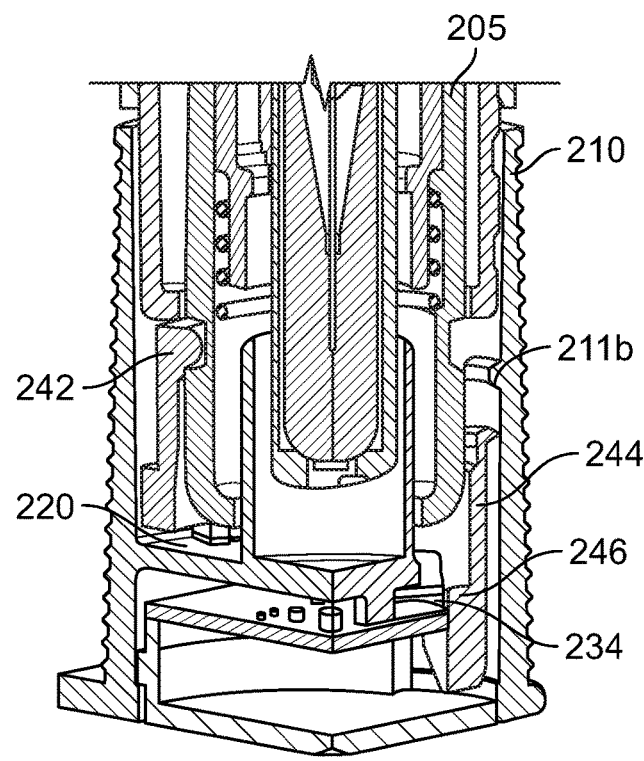

Upon beginning removal of the cap 210 to a first position and as illustrated in FIG. 17, the activation mechanism 240 remains engaged with the needle guard 205. However, the coupling between the housing 202 and the cap 210 disengages, thus allowing for the cap 210 to be removed. At this step, a tab 246 (having a first surface 248 and an angled surface 250) of the finger 244 contacts the rotating switch 234 in a similar manner to the configuration described with reference to FIGS. 9 and 11.

Figure 18:
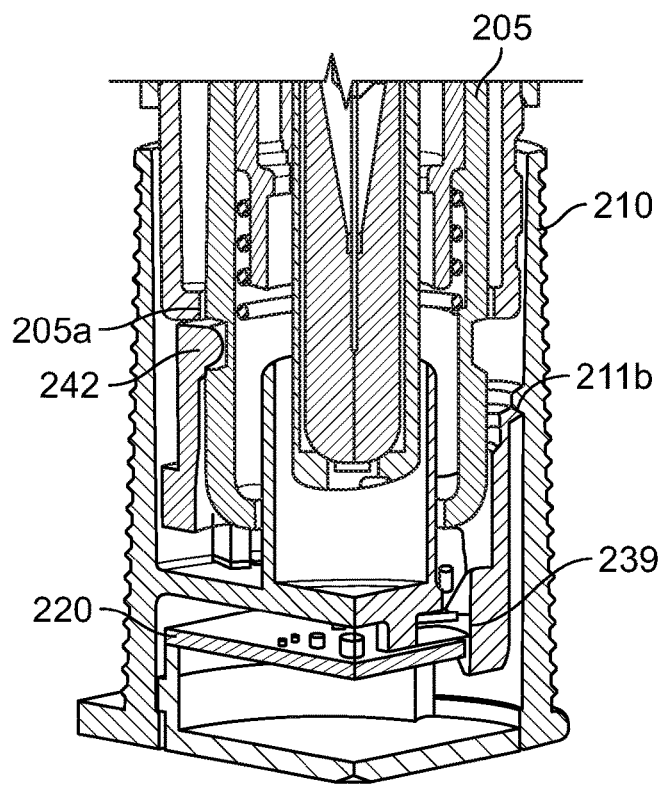
Figure 19:
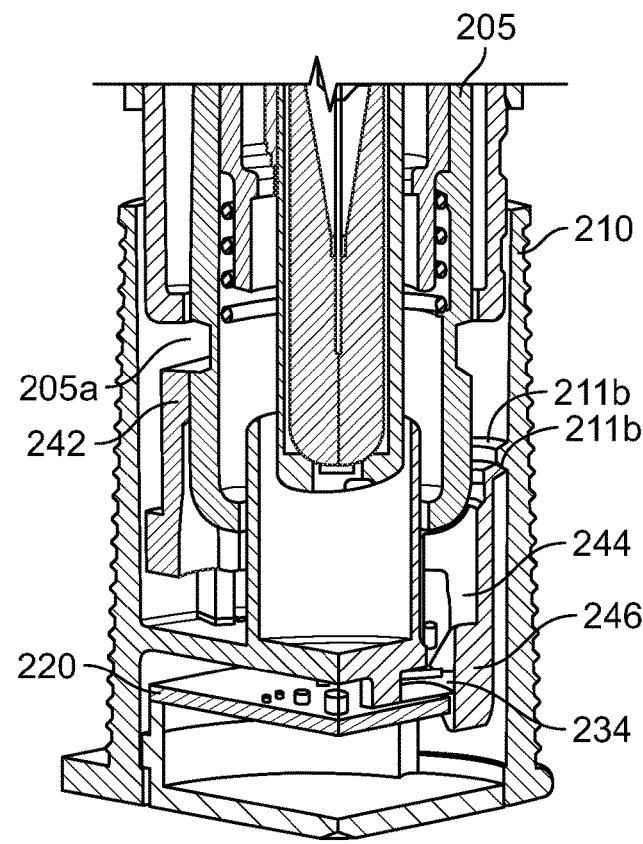
Figure 20:
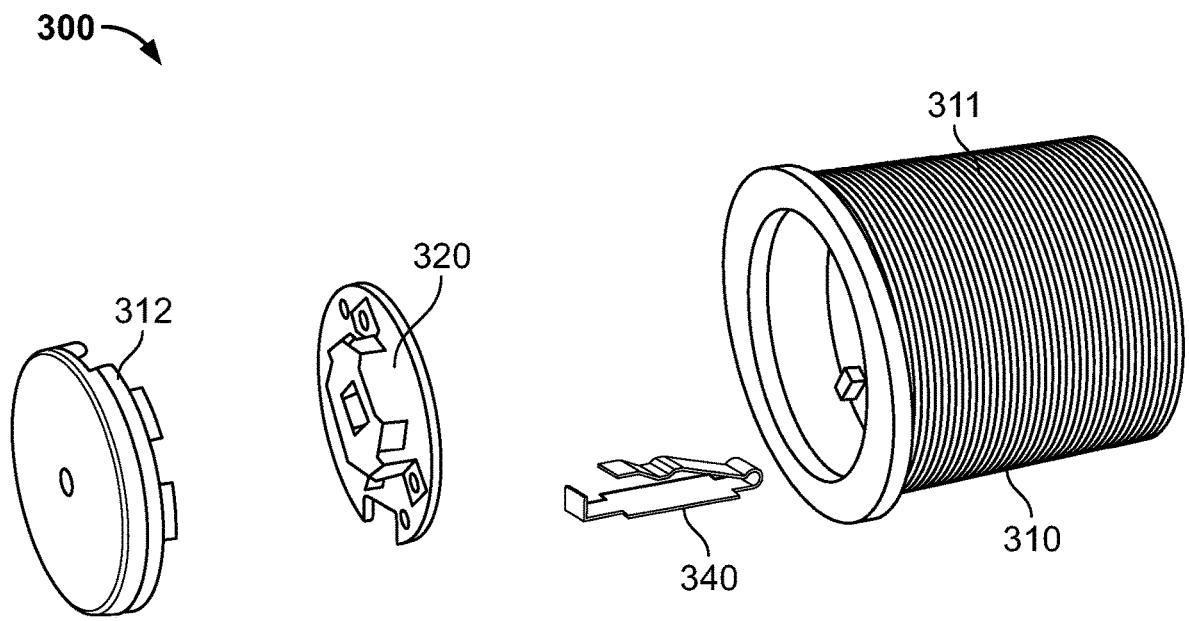
FIG. 20 illustrates a perspective view of an alternate removable cap for the drug delivery device in accordance with various embodiments.
Figure 21:
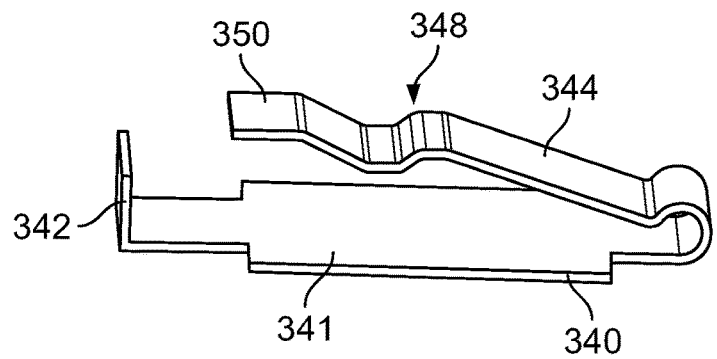
FIG. 21 illustrates a perspective view of an alternate activation mechanism for the drug delivery device in accordance with various embodiments.

As illustrated in FIG. 18, continued removal of the cap 210 causes the activation mechanism 240 to engage a catching protrusion 211b of the cap 210. At this point, the activation mechanism 240 fully depresses the rotating switch 234, thereby activating the electronic component 220. As illustrated in FIG. 19, by engaging the catching protrusion 211b of the cap 210, the activation mechanism 240 becomes fixed to the cap 210. Accordingly, the locking protrusion 242 deforms and disengages from the channel 205a of the needle guard 205. As such, the cap 210, the electronic component 220 including the rotatable switch assembly 230, and the activation mechanism 240 are removed from the housing 202, and because the activation mechanism 240 remains in contact with the rotating switch 234, the electronic component remains powered and activated.

As illustrated in FIGS. 20-23, an alternate drug delivery device 300 is provided. The drug delivery device 300 includes similar features and elements as the drug delivery devices 100 and 200 of FIGS. 1-19, and thus have reference numerals with identical two-digit suffixes as those in the drug delivery devices 100 and 200. As such, for the sake of brevity, similar components will not be described in detail.

In this example, the alternate drug delivery device 300 includes an activation mechanism 340 in the form of a spring lever. The activation mechanism 340 includes a body portion 341, a coupling tab 342 extending inwardly from the body portion 341, and an activation lever 344 extending from the body portion 341. A facing surface 350 of the activation lever 344 interacts with the rotating switch 334 to selectively power the electronic component 320. The activation mechanism 340 may further include a bent portion 348 to provide clearance from other components disposed in the cap 310. The activation mechanism 340 may be constructed of a resilient material such as steel or other suitable metals.

The coupling tab 342 is disposed near the cover member 312 and is used to secure the activation mechanism 340 in the cap 310. It is understood that any number of approaches may be used to secure the activation mechanism 340 in the cap, such as, for example, a press fit, an interlocking coupling, an opening and corresponding protrusion, and the like.

Figure 22:
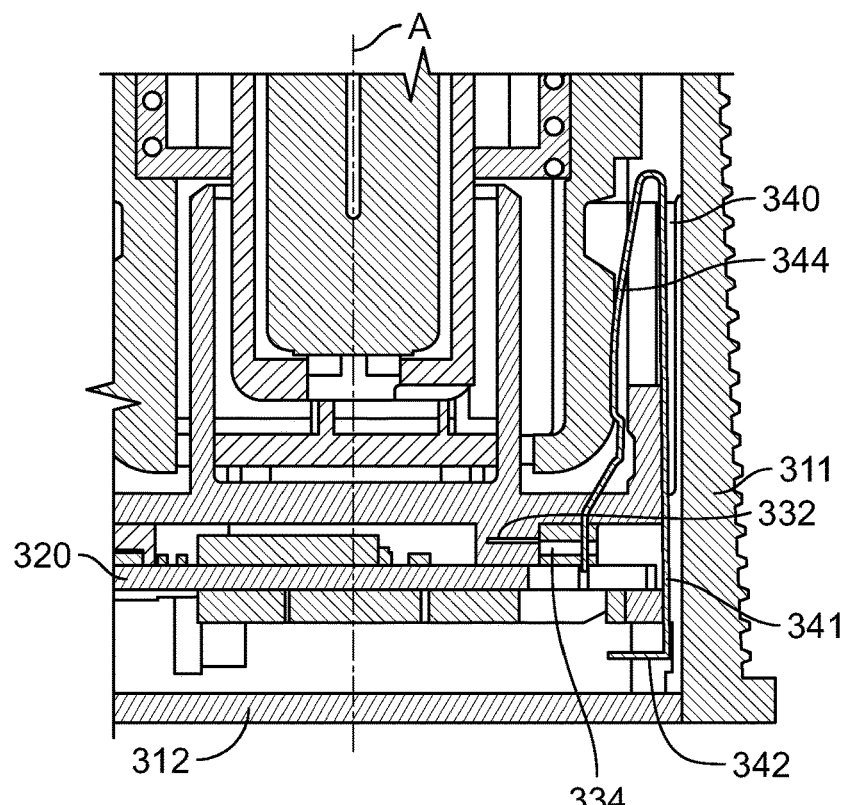
FIGS. 22 & 23 illustrate perspective views of the drug delivery device of FIGS. 20 and 21 during removal of the removable cap in accordance with various embodiments.
Figure 23:
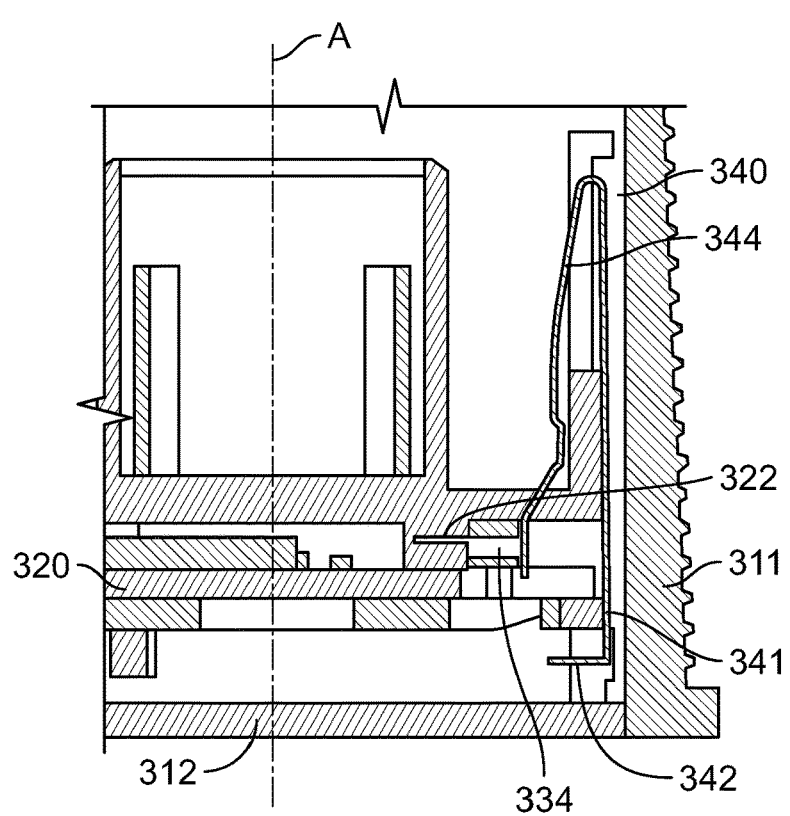

As illustrated in FIG. 22, prior to cap removal, the activation lever 344 contacts and biases the needle guard such that the facing surface 350 is displaced away from the rotating switch 334. In this configuration, the activation mechanism 340 is in a compressed or loaded configuration. As such, the rotating switch assembly 330 is in a disengaged configuration. When the cap 310 is removed from the housing (not shown), and as illustrated in FIG. 23, the activation lever 340 is urged to an unloaded, relaxed state where the activation lever 344 is inwardly displaced. So configured, the facing surface 350 moves inwards and contacts the rotating switch 334 to cause rotation into the switch body 332, thereby activating the rotating switch assembly 330 to power the electronic component 320.

So configured, the drug delivery device is activated by converting the axial motion from removing the cap to motion in an orthogonal plane to the central longitudinal axis. Accordingly, a compact switch assembly may be used which does not occupy substantial space and does not require a high activation force beyond the force required to remove the cap from the housing. Further, by using an entirely passive design, there is no additional user interaction necessary to activate the electronics beyond the current requirement of only removing the cap prior to administration of the drug.

While the foregoing description provides multiple different "embodiments" for the type of actuating mechanisms that may be incorporated into the electronic systems disclosed herein, it should be appreciated that the different actuating mechanisms could also be combined with each other, as desired. That is, a person of ordinary skill would understand that a locking actuating mechanism (e.g., FIGS. 14-19) could be combined with a spring lever actuating mechanism disclosed herein (e.g., FIGS. 20-23).

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a syringe barrel. In some instances, the syringe barrel is a primary container that is either filled or pre-filled for treatment with the medicament. The primary container can be a cartridge or a pre-filled syringe.

For example, the drug delivery device or more specifically the syringe barrel of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Figure 2:
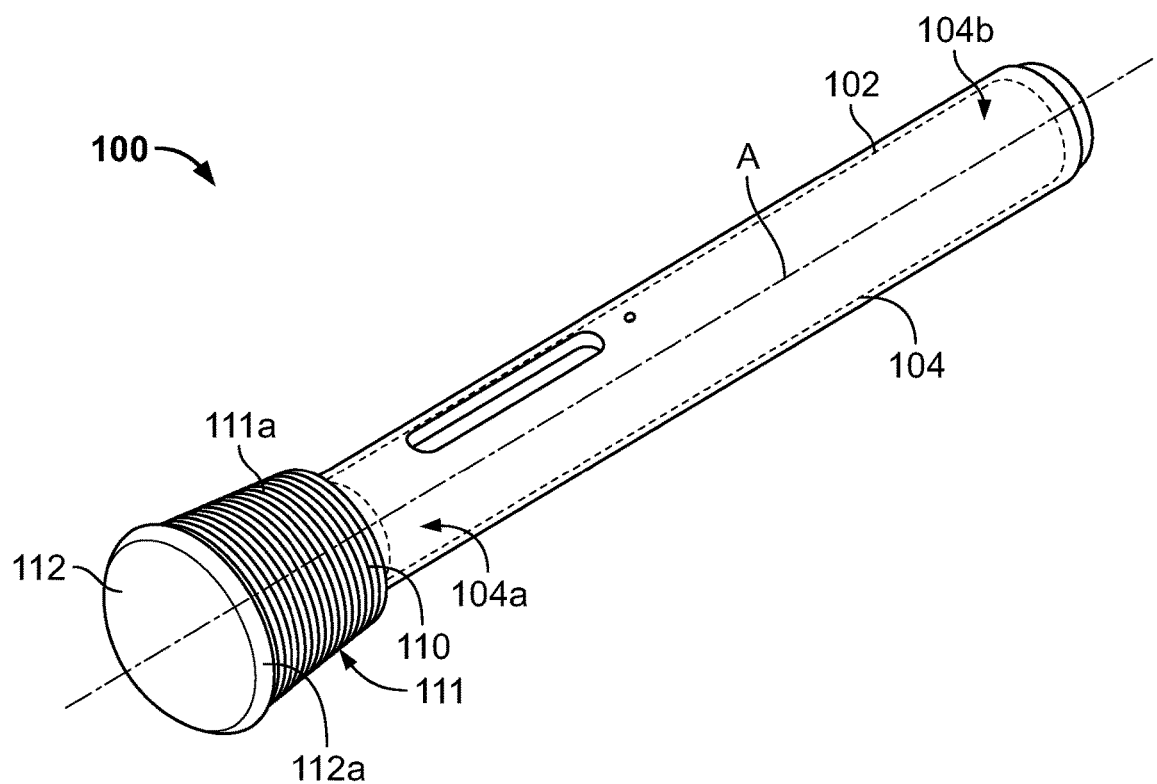
FIG. 2 illustrates a perspective view of an example electronic drug delivery device in accordance with various embodiments.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated by reference herein in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1$a$); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-$B.$ $anthracis$ protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab);

M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug injection device, actuation mechanisms, systems, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the device, drive damper mechanisms, systems, methods, and their elements.

What is claimed is:

1. A drug delivery device comprising:
  a housing;
  a drug delivery assembly at least partially disposed within the housing along a longitudinal axis, the drug delivery assembly having a first end and a second end;
  a cap defining a shell and being adapted to removably couple to the housing and at least partially cover a portion of the first end of the drug delivery assembly;
  at least one electronic component at least partially disposed in and coupled to the cap, and
  a power source at least partially disposed in and coupled to the cap for selectively powering the at least one electronic component;
  a switch assembly operably coupled between the at least one electronic component and the power source, the switch assembly being movable along a plane orthogonal to the longitudinal axis of the drug delivery assembly to cause the power source to provide power to the at least one electronic component; and an activation mechanism at least partially disposed in the cap, the activation mechanism comprising a sliding activation ring having a finger portion;

wherein upon urging the cap along the longitudinal axis in a direction away from the housing, the finger portion of the activation mechanism engages the switch assembly and causes the switch assembly to move, thereby causing the power source to provide power to the at least one electronic component, wherein upon urging the cap along the longitudinal axis to a first position, the switch assembly moves relative to the finger portion to engage the finger portion, and wherein upon urging the cap along the longitudinal axis to a second position, the sliding activation ring engages a cap coupling portion disposed on the cap to be removed from the housing with the cap.

2. The drug delivery device of claim 1, wherein the finger portion of the sliding activation ring comprises a chamfered engaging surface that engages the switch assembly.

3. The drug delivery device of claim 1, wherein the cap coupling portion comprises a protrusion disposed on an inner surface of the cap.

4. The drug delivery device of claim 1, wherein the sliding activation ring engages a portion of the drug delivery assembly to prevent the drug delivery assembly from discharging while the cap at least partially covers a portion of the first end of the drug delivery assembly.

5. A signal cap for an autoinjector comprising:
a cap body defining a cap shell and being formed along a longitudinal axis;
at least one electronic component at least partially disposed in and coupled to the cap shell,
a power source at least partially disposed in and coupled to the cap shell for selectively powering the at least one electronic component;
a switch assembly operably coupled between the at least one electronic component and the power source, the switch assembly being movable along a plane orthogonal to the longitudinal axis of the cap body to cause the power source to provide power to the at least one electronic component; and an activation mechanism at least partially disposed in the cap shell, the activation mechanism comprising a sliding activation ring having a finger portion;

wherein upon urging the cap body along the longitudinal axis to a first position, the finger portion of the activation mechanism engages the switch assembly and causes the switch assembly to move relative to the finger portion to engage the finger portion, thereby causing the power source to provide power to the at least one electronic component, and upon urging the cap to a second position, the sliding activation ring engages a cap coupling portion to move with the cap.

6. The signal cap of claim 5, wherein the finger portion of the sliding activation ring comprises a chamfered engaging surface that engages the switch assembly.

7. The signal cap of claim 5, wherein the cap coupling portion comprises a protrusion disposed on an inner surface of the cap.

8. The signal cap of claim 5, wherein the sliding activation ring engages a portion of the drug delivery assembly to prevent a drug delivery device from discharging while the cap is coupled to the drug delivery device.

9. An activation mechanism for a drug delivery device, the activation mechanism comprising:
a sliding activation ring;
a finger portion having a first end and a second end, the first end being coupled to the sliding activation ring such that the finger portion extends therefrom along a longitudinal direction, the second end of the finger portion including a tab having a chamfered engaging surface and a retaining surface positioned adjacent to the chamfered engaging surface;
wherein when the activation mechanism is disposed in a drug delivery device cap, the chamfered engaging surface of the tab of the finger portion engages and causes movement of a switch assembly to cause a power source to provide power to an electronic component and the retaining surface retains the switch assembly in a position that causes the power source to continue providing power to the electronic component, wherein upon urging the drug delivery device cap to a second position, the sliding activation ring engages a cap coupling portion to move therewith.

* * * * *